United States Patent
Laas

(10) Patent No.: US 10,221,199 B2
(45) Date of Patent: Mar. 5, 2019

(54) ISOCYANATOSILANES WITH THIOURETHANE STRUCTURE

(71) Applicant: Covestro Deutschland AG, Leverkusen (DE)

(72) Inventor: Hans-Josef Laas, Odenthal (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/398,305

(22) Filed: Jan. 4, 2017

(65) Prior Publication Data

US 2017/0114082 A1 Apr. 27, 2017

Related U.S. Application Data

(63) Continuation of application No. 14/425,103, filed as application No. PCT/EP2013/067939 on Aug. 29, 2013, now Pat. No. 9,637,506.

(30) Foreign Application Priority Data

Sep. 4, 2012 (EP) ..................................... 12182885

(51) Int. Cl.
| | |
|---|---|
| *C07F 7/08* | (2006.01) |
| *C07F 7/18* | (2006.01) |
| *C08G 18/73* | (2006.01) |
| *C08G 18/75* | (2006.01) |
| *C08G 18/28* | (2006.01) |
| *C08G 18/38* | (2006.01) |
| *C08G 18/71* | (2006.01) |
| *C08G 18/72* | (2006.01) |

(52) U.S. Cl.
CPC ............ *C07F 7/081* (2013.01); *C07F 7/1804* (2013.01); *C08G 18/289* (2013.01); *C08G 18/3893* (2013.01); *C08G 18/718* (2013.01); *C08G 18/72* (2013.01); *C08G 18/73* (2013.01); *C08G 18/755* (2013.01); *C08G 18/758* (2013.01)

(58) Field of Classification Search
CPC ..... C07F 7/0818; C07F 7/1836; C08G 18/289
See application file for complete search history.

(56) References Cited

U.S. PATENT DOCUMENTS

| | | | |
|---|---|---|---|
| 3,149,139 A * | 9/1964 | Meisert | .......................... 252/404 |
| 3,494,951 A | 2/1970 | Berger | |
| 3,627,722 A | 12/1971 | Seiter | |
| 4,031,120 A * | 6/1977 | Gervase | ............... C08G 18/289 106/287.11 |
| 4,246,369 A | 1/1981 | McGinniss et al. | |
| 5,364,955 A | 11/1994 | Zwiener et al. | |
| 5,756,751 A | 5/1998 | Schmalstieg et al. | |
| 6,515,096 B2 | 2/2003 | Windmueller et al. | |
| 8,658,752 B2 | 2/2014 | Groenewolt et al. | |
| 2008/0092539 A1 | 4/2008 | Marshall et al. | |
| 2011/0082254 A1 | 4/2011 | Sepeur et al. | |

FOREIGN PATENT DOCUMENTS

| | | |
|---|---|---|
| DE | 2540080 A1 | 3/1976 |
| EP | 0070475 A2 | 1/1983 |
| EP | 0202491 A2 | 11/1986 |
| EP | 0372561 A2 | 6/1990 |
| EP | 0596360 A1 | 5/1994 |
| EP | 0 649 850 A1 | 4/1995 |
| EP | 0807649 A1 | 11/1997 |
| EP | 1136495 A2 | 9/2001 |
| GB | 1526953 A | 10/1978 |
| JP | S60233133 A | 11/1985 |
| JP | 61047774 A | 3/1986 |
| JP | S61218631 A | 9/1986 |
| WO | WO-2009/115079 A1 | 9/2009 |
| WO | WO-2009156148 A1 | 12/2009 |

OTHER PUBLICATIONS

International Search Report for PCT/EP2013/067939 dated Oct. 15, 2013.

* cited by examiner

*Primary Examiner* — Kuo Liang Peng
(74) *Attorney, Agent, or Firm* — Drinker Biddle & Reath LLP

(57) ABSTRACT

The invention relates to a method for producing compounds containing isocyanate and silane groups by reacting at least A) one monomeric diisocyanate containing aliphatically, cycloaliphatically, araliphatically and/or aromatically bonded isocyanate groups with B) a mercaptosilane, characterized in that component A) is reacted with component B) in an equivalent ratio of isocyanate groups to mercapto groups of at least 06:01 to at most 40:1. Furthermore, the invention relates to the products which can be obtained using the method according to the invention, and to a composition containing compounds that contain isocyanate and silane groups. Moreover, the invention relates to the use of the products which can be obtained using the method according to the invention and the composition according to the invention as starting components in the production of silane group-containing polyurethanes, cross-linkable binders, varnish, and raw materials for sealants or adhesives.

7 Claims, No Drawings

ISOCYANATOSILANES WITH THIOURETHANE STRUCTURE

CROSS-REFERENCE TO RELATED APPLICATIONS

This application is a continuation of U.S. patent application Ser. No. 14/425,103, which is a national stage application (under 35 U.S.C. § 371) of PCT/EP2013/067939, filed Aug. 29, 2013, which claims benefit of European Application No. 12182885.9, filed Sep. 4, 2012, both of which are incorporated herein by reference in their entirety.

The invention relates to a process for preparing compounds containing isocyanate groups and silane groups, to the products obtainable by this process and to a composition comprising compounds containing isocyanate groups and silane groups. The invention further relates to the use of the products obtainable by the process according to the invention and of the composition of compounds containing isocyanate groups and silane groups as a starting component in the preparation of polyurethanes containing silane groups, and in the production of crosslinkable binders and of raw materials for varnishes, sealants or adhesives.

Isocyanatoorganosilanes, being compounds having two different reactive functionalities, are units of interest for chemical synthesis. They can react either with compounds bearing acidic hydrogen atoms via the isocyanate group or, for example in the presence of moisture, crosslink under polycondensation of the silane group. Isocyanatoorganosilanes are of particular significance for modification of hydroxy-functional polymers for a number of different applications.

Isocyanatoalkylalkoxysilanes, as described, for example, in U.S. Pat. No. 3,494,951 or EP-A 0 649 850, enable, for example, the preparation of particularly low-viscosity silane-terminated prepolymers which are used as moisture-crosslinking adhesives and sealants (see, for example, EP-A 0 070 475, EP-A 0 372 561).

According to the teaching of WO 2009/115079, alkoxysilane-containing reaction products of polyols, for example polyacrylate polyols and/or simple polyhydric alcohols, with isocyanatopropyltrimethoxysilane or isocyanatopropyltriethoxysilane can be cured thermally in the presence of suitable catalysts even with exclusion of water. Binders of this kind enable, inter alia, the formulation of automotive paints of very high scratch resistance.

However, the industrial processes for preparing isocyanatoalkylalkoxysilanes are very inconvenient and costly. The products are obtained in only moderate yields and, moreover, with varying quality and inadequate storage stability. Efforts have therefore already been made to synthesize alternative compounds which have both an isocyanate group and a silane structure.

EP-A 1 136 495 describes a process for preparing low-monomer 1:1 mono adducts from specific secondary aminoalkylalkoxysilanes and diisocyanates, in which the co-reactants are reacted with one another using a large molar excess of isocyanate and, thereafter, the unconverted monomeric diisocyanates are removed by distillation. Aminosilanes used in this process are the aspartic esters which are known from EP-A 0 596 360, are obtainable by reaction of dialkyl maleates and aminosilanes and, according to the teaching of EP-A 1 136 495, form storage-stable adducts with isocyanates, in contrast to other simple secondary aminosilanes. As shown by in-house studies, the urea structures formed in the reaction of the silane-functional aspartic esters with isocyanates are indeed stable to redissociation, while simple N-alkylaminosilanes, with respect to isocyanate groups, act like standard blocking agents and are released again at elevated temperature.

During the thin-film distillation of reaction mixtures based on such simple N-alkylaminosilanes, even if a very high excess of diisocyanate has been chosen at the start, thermal urea cleavage and subsequently recombination, given that diisocyanate monomer has already partly distilled off, cause formation not only of the desired isocyanatosilane (1:1 mono adduct) but also of very high proportions of disilylated bisurea (2:1 bis adduct) as an unwanted by-product, which is no longer available for further conversion.

Even though the reaction, described in EP-A 1 136 495, of diisocyanates with silane-functional aspartic esters, in contrast, gives urea groups which are stable to redissociation under the conditions of a thin-film distillation, this process has another serious disadvantage.

As known from EP-A 0 807 649, adducts of isocyanates onto aspartic esters containing alkoxysilane groups react even at comparatively mild temperatures of 50-160° C., with elimination of the alcohol from one of the ester groups and cyclization, to give hydantoin derivatives. This reaction inevitably also takes place in the process of EP-A 1 136 495 because of the thermal stress during the thin-film distillation. The monoalcohol released either reacts with the desired isocyanatosilane with urethanization and loss of NCO functionality in the target molecule or is distilled out of the product together with excess monomeric diisocyanate. The resultant diisocyanate distillate contaminated by the alcohol or by the urethane that forms cannot be reused in the synthesis process without further purification and may need to be disposed of in a costly manner.

A further method already known in principle for preparation of isocyanates containing silane groups is that of reacting polyisocyanates with mercaptosilanes. JP-A 60233133 describes, for example, the equimolar reaction of hexamethylene diisocyanate (HDI) with 3-mercaptopropyltrimethoxysilane. The reaction product which, as well as the 1:1 adduct, because of the statistical course of the reaction, contains considerable proportions of 2:1 bis adduct and monomeric, unconverted diisocyanate is used as such without further purification or monomer removal for modification of a polyamide. JP-A 61047774 describes the use of these reaction products as formation components for hotmelt adhesives.

JP-A 61218631 also describes the use of reaction products of diisocyanates and mercaptosilanes for hotmelt adhesives. The reaction mixtures obtained through the equimolar reaction of diisocyanates and mercaptosilanes serve here for modification of polyester resins.

DE-A 2540080 describes the use of different isocyanatosilanes, including adducts of polyisocyanates and silanes that are reactive toward isocyanate groups, for example including mercaptosilanes, in a ratio of equivalents of isocyanate groups to groups that are reactive toward isocyanates of at least 2:1, in specific adhesive compositions. In the specific examples of DE-A 2540080, however, isocyanatosilanes based on mercaptosilanes are not used.

U.S. Pat. No. 4,246,369, however, discloses that aliphatic and aromatic thiols are blocking agents for isocyanates, which are eliminated again at only low temperatures.

There was therefore a need for novel isocyanatosilanes, especially thermally stable isocyanatosilanes, which can be prepared in a simple process.

It was therefore an object of the present invention to provide a process for preparing thermally stable and storage-stable isocyanatosilanes, which is based on raw materials of good availability and is additionally economically viable. Through the process according to the invention, the desired products should be preparable in a reliable and reproducible manner and without excessively large proportions of unwanted by-products.

This object is achieved in accordance with the invention by a process for preparing compounds containing isocyanate groups and silane groups, by reacting at least A) a monomeric diisocyanate having aliphatically, cycloaliphatically, araliphatically and/or aromatically bonded isocyanate groups with B) a mercaptosilane, characterized in that component A) is reacted with component B) in a ratio of equivalents of isocyanate groups to mercapto groups of at least 6:1 to at most 40:1.

The process according to the invention is based on the surprising observation that thiourethanes formed from standard mercaptoalkylsilanes and diisocyanates, unlike the above-described N-alkylaminosilanes, are entirely stable under the conditions of a thin-film distillation. The person skilled in the art was unable to take any hint at all from any of the abovementioned publications that it is possible, in spite of the known thermal lability of thiourethanes, to work up reaction mixtures of diisocyanates and mercaptosilanes by distillation without breakdown; U.S. Pat. No. 4,246,369 even teaches that the opposite is the case. This surprising stability of thiourethane formation allows simple distillation of the unconverted monomers out of the desired isocyanatosilane (1:1 mono adduct) in reaction mixtures of mercaptosilanes and molar excess amounts of diisocyanates, without formation of an increased proportion of 2:1 bis adduct at the same time. Thus, it is also possible to achieve reactions with ratios of equivalents of isocyanate groups to mercapto groups of 6:1 to 40:1. Within this range, it is possible to reduce the formation of unwanted 2:1 bis adduct to an economically acceptable proportion and nevertheless to achieve sufficient conversion.

In a preferred embodiment of the invention, mercaptosilanes of the general formula (I) or mixtures thereof are used as component B)

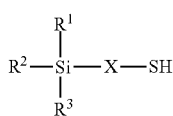

(I)

in which $R^1$, $R^2$ and $R^3$ are identical or different radicals and each is a saturated or unsaturated, linear or branched, aliphatic or cycloaliphatic radical or an optionally substituted aromatic or araliphatic radical having up to 18 carbon atoms, which may optionally contain up to 3 heteroatoms from the group of oxygen, sulfur, nitrogen, and X is a linear or branched organic radical having at least 2 carbon atoms.

Particularly preferred mercaptosilanes B) for the process according to the invention are those of the general formula (I) in which $R^1$, $R^2$ and $R^3$ are identical or different radicals and each is a saturated, linear or branched, aliphatic or cycloaliphatic radical having up to 6 carbon atoms, which may optionally contain up to 3 oxygen atoms and X is a linear or branched alkylene radical having 2 to 10 carbon atoms.

Very particularly preferred mercaptosilanes B) are those of the general formula (I) in which $R^1$, $R^2$ and $R^3$ are each alkyl radicals having up to 6 carbon atoms and/or alkoxy radicals containing up to 3 oxygen atoms, with the proviso that at least one of the $R^1$, $R^2$ and $R^3$ radicals is such an alkoxy radical and X is a propylene radical (—$CH_2$—$CH_2$—$CH_2$—).

Further preferred mercaptosilanes B) are those of the general formula (I) in which $R^1$, $R^2$ and $R^3$ are identical or different radicals and each is methyl, methoxy or ethoxy, with the proviso that at least one of the $R^1$, $R^2$ and $R^3$ radicals is a methoxy or ethoxy radical and X is a propylene radical (—$CH_2$—$CH_2$—$CH_2$—).

Suitable mercaptosilanes B) are, for example, 2-mercaptoethyltrimethylsilane, 2-mercaptoethylmethyldimethoxysilane, 2-mercaptoethyltrimethoxysilane, 2-mercaptoethyltriethoxysilane, 3-mercaptopropylmethyldimethoxysilane, 3-mercaptopropyldimethylmethoxysilane, 3-mercaptopropyltrimethoxysilane, 3-mercaptopropylmethyldiethoxysilane, 3-mercaptopropyltriethoxysilane, 3-mercaptopropylethyldimethoxysilane, 3-mercaptopropylethyldiethoxysilane and/or 4-mercaptobutyltrimethoxysilane.

Suitable starting compounds A) for the process according to the invention are any desired diisocyanates which have aliphatically, cycloaliphatically, araliphatically and/or aromatically ring bonded isocyanate groups and can be prepared by any desired processes, for example by phosgenation or by a phosgene-free route, for example by urethane cleavage.

Preferred diisocyanates are, for example, those of the general formula (II)

$$OCN—Y—NCO \qquad (II)$$

in which Y is a linear or branched, aliphatic or cycloaliphatic radical having 4 to 18 carbon atoms or an optionally substituted aromatic or araliphatic radical having 6 to 18 carbon atoms.

Suitable examples are 1,4-diisocyanatobutane, 1,6-diisocyanatohexane (HDI), 1,5-diisocyanato-2,2-dimethylpentane, 2,2,4- or 2,4,4-trimethyl-1,6-diisocyanatohexane, 1,10-diisocyanatodecane, 1,3- and 1,4-diisocyanatocyclohexane, 1,4-diisocyanato-3,3,5-trimethylcyclohexane, 1,3-diisocyanato-2-methylcyclohexane, 1,3-diisocyanato-4-methylcyclohexane, 1-isocyanato-3,3,5-trimethyl-5-isocyanatomethylcyclohexane (isophorone diisocyanate; IPDI), 1-isocyanato-1-methyl-4(3)-isocyanatomethylcyclohexane, 2,4'- and 4,4'-diisocyanatodicyclohexylmethane ($H_{12}$-MDI), 1,3- and 1,4-bis(isocyanatomethyl)cyclohexane, 4,4'-diisocyanato-3,3'-dimethyldicyclohexylmethane, 4,4'-diisocyanato-3,3',5,5'-tetramethyldicyclohexylmethane, 4,4'-diisocyanato-1,1'-bi(cyclohexyl), 4,4'-diisocyanato-3,3'-dimethyl-1,1'-bi(cyclohexyl), 4,4'-diisocyanato-2,2',5,5'-tetramethyl-1,1'-bi(cyclohexyl), 1,8-diisocyanato-p-menthane, 1,3-diisocyanatoadamantane, 1,3-dimethyl-5,7-diisocyanatoadamantane, 1,3- and 1,4-bis(isocyanatomethyl)benzene, 1,3- and 1,4-bis(1-isocyanato-1-methylethyl)benzene (TMXDI), bis(4-(1-isocyanato-1-methylethyl)phenyl) carbonate, phenylene 1,3- and 1,4-diisocyanate, tolylene 2,4- and 2,6-diisocyanate and any desired mixtures of these isomers, diphenylmethane 2,4'- and/or 4,4'-diisocyanate and naphthylene 1,5-diisocyanate and any desired mixtures of such diisocyanates. Further diisocyanates that are likewise suitable can additionally be found, for example, in Justus Liebigs Annalen der Chemie, volume 562 (1949) p. 75-136.

Preferred starting components A) are diisocyanates of the general formula (II) in which Y is a linear or branched, aliphatic or cycloaliphatic radical having 6 to 13 carbon atoms.

Particularly preferred starting components A) for the process according to the invention are 1,6-diisocyanatohexane, 1-isocyanato-3,3,5-trimethyl-5-isocyanatomethylcyclohexane, 2,4'- and/or 4,4'-diisocyanatodicyclohexylmethane or any desired mixtures of these diisocyanates.

To perform the process according to the invention, the diisocyanates A) are reacted with the mercaptosilanes B) at temperatures of 20 to 200° C., preferably 40 to 160° C. This is done by using components A) and B) in a ratio of equivalents of isocyanate groups (component A) to mercapto groups (component B) of at least 6:1 to at most 40:1, preferably of 8:1 to at most 30:1 and more preferably of 10:1 to at most 25:1.

The reaction of the starting components A) and B) in the process according to the invention can be executed in solution or without solvent in substance, but is preferably executed without solvent.

The process of the invention can be performed without the use of catalysts. The reaction can optionally also be accelerated using customary catalysts known from polyurethane chemistry. Examples include tertiary amines, for example triethylamine, tributylamine, dimethylbenzylamine, diethylbenzylamine, pyridine, methylpyridine, dicyclohexylmethylamine, dimethylcyclohexylamine, N,N,N',N'-tetramethyldiaminodiethyl ether, bis(dimethylaminopropyl)urea, N-methyl- or N-ethylmorpholine, N-cocomorpholine, N-cyclohexylmorpholine, N,N,N',N'-tetramethylethylenediamine, N,N,N',N'-tetramethyl-1,3-butanediamine, N,N,N',N'-tetramethyl-1,6-hexanediamine, pentamethyldiethylenetriamine, N-methylpiperidine, N-dimethylaminoethylpiperidine, N,N'-dimethylpiperazine, N-methyl-N'-dimethylaminopiperazine, 1,2-dimethylimidazole, 2-methylimidazole, N,N-dimethylimidazole-β-phenylethylamine, 1,4-diazabicyclo[2.2.2]octane (DABCO) and bis(N,N-dimethylaminoethyl) adipate, amidines, for example 1,5-diazabicyclo[4.3.0]nonene (DBN), 1,8-diazabicyclo[5.4.0]undec-7-ene (DBU) and 2,3-dimethyl-3,4,5,6-tetrahydropyrimidine, alkanolamine compounds, for example triethanolamine, triisopropanolamine, N-methyldiethanolamine, N-ethyldiethanolamine, dimethylaminoethanol and 2-(N,N-dimethylaminoethoxy)ethanol, N,N',N''-tris(dialkylaminoalkyl)hexahydrotriazines, for example N,N',N''-tris(dimethylaminopropyl)-s-hexahydrotriazine, bis(dimethylaminoethyl) ether and metal salts, for example inorganic and/or organic compounds of iron, lead, bismuth, zinc and/or tin in customary oxidation states of the metal, for example iron(II) chloride, iron(III) chloride, bismuth(III) bismuth(III) 2-ethylhexanoate, bismuth(III) octoate, bismuth(III) neodecanoate, zinc chloride, zinc 2-ethylcaproate, tin(II) octoate, tin(II) ethylcaproate, tin(II) palmitate, dibutyltin(IV) dilaurate (DBTL), dibutyltin(IV) dichloride or lead octoate.

Preferred catalysts for use are tertiary amines, amidines and tin compounds of the type specified.

Particularly preferred catalysts are 1,4-diazabicyclo[2.2.2]octane (DABCO), 1,5-diazabicyclo[4.3.0]nonene (DBN), 1,8-diazabicyclo[5.4.0]undec-7-ene (DBU) and dibutyltin(IV) dilaurate (DBTL).

The catalysts mentioned by way of example can be used individually or in the form of any desired mixtures with one another in the preparation of the inventive isocyanatosilanes and are used, if at all, in amounts of 0.001% to 1.0% by weight, preferably 0.01% to 0.5% by weight, calculated as the total amount of catalysts used, based on the total amount of the starting compounds used.

The progress of the reaction in the process according to the invention can be monitored by determining the NCO content by titrimetric means, for example. On attainment of the desired NCO content, generally after full urethanization, the reaction is stopped.

In a preferred embodiment of the invention, after the reaction of components A) with B), any unconverted excess of monomeric diisocyanates A) is separated from the reaction product apart from a residual content of less than 1% by weight, preferably of less than 0.5% by weight, more preferably of less than 0.3% by weight, based on the total mass of the reaction product.

This is preferably done by freeing the reaction mixture of excess monomeric diisocyanates by thin-film distillation under reduced pressure, for example at a pressure of below 1.0 mbar, preferably below 0.5 mbar, more preferably below 0.2 mbar, under very gentle conditions, for example at a temperature of 100 to 200° C., preferably of 120 to 180° C.

The distillates obtained can be used without any problem for another reaction with mercaptosilanes.

In a further, although less preferred embodiment of the process according to the invention, the monomeric isocyanates are separated from the thiourethane formed by extraction with suitable solvents inert toward isocyanate and silane groups, for example aliphatic or cycloaliphatic hydrocarbons such as pentane, hexane, heptane, cyclopentane or cyclohexane.

Irrespective of the type of workup, the products of the process according to the invention obtained are clear, virtually colorless compounds containing isocyanate and silane groups, which, depending on the starting diisocyanate chosen, are liquids of low to high viscosity and have NCO contents of 6.0% to 13.5% by weight, preferably 7.0% to 12.0% by weight, more preferably 8.0% to 11.5% by weight, and residual contents of monomeric starting diisocyanates of less than 1.0% by weight, preferably of less than 0.5% by weight, more preferably of less than 0.3% by weight, based on the total mass of the reaction product.

The invention likewise provides a composition comprising a) compounds of the general formula (III) containing isocyanate groups and silane groups,

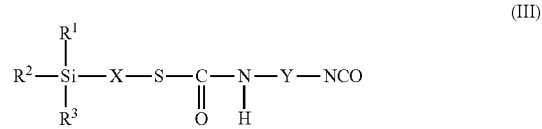

b) compounds of the general formula (IV) containing silane groups

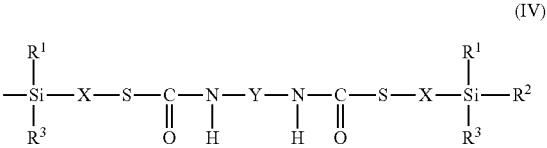

and c) monomeric diisocyanates having aliphatically, cycloaliphatically, araliphatically and/or aromatically bonded isocyanate groups, where R¹, R² and R³ are identical or different radicals and each is a saturated or unsaturated, linear or branched, aliphatic or cycloaliphatic radical or an optionally substituted aromatic or araliphatic radical having up to 18 carbon atoms, which may optionally contain up to 3 heteroatoms from the group of oxygen, sulfur, nitrogen, X is a linear or branched organic radical having at least 2 carbon atoms and Y is a linear or branched, aliphatic or cycloaliphatic radical having 4 to 18 carbon atoms or an optionally substituted aromatic or araliphatic radical having 6 to 18 carbon atoms.

characterized in that component a) makes up a proportion of ≥85% by weight, preferably ≥90% by weight, component b) a proportion of ≤15% by weight, preferably ≤10% by weight, of the total mass of components a) and b), and component c) makes up ≤1% by weight of the overall composition.

In a preferred embodiment of the invention, component b) makes up a proportion of 2% to 15% by weight, preferably 2% to 10% by weight, of the total mass of components a) and b).

Preferably, in the formulae (III) and (IV),

R¹, R² and R³ are identical or different radicals which are each a saturated, linear or branched, aliphatic or cycloaliphatic radical having up to 6 carbon atoms, which may optionally contain up to 3 oxygen atoms and X is a linear or branched alkylene radical having 2 to 10 carbon atoms.

More preferably, in the formulae (III) and (IV),

R¹, R² and R³ are identical or different radicals which are each an alkyl radical having up to 6 carbon atoms and/or alkoxy radicals containing up to 3 oxygen atoms, with the proviso that at least one of the R¹, R² and R³ radicals is such an alkoxy radical and X is a propylene radical (—CH$_2$—CH$_2$—CH$_2$—).

Most preferably, in the formulae (III) and (IV),

R¹, R² and R³ are identical or different radicals which are each methyl, methoxy or ethoxy, with the proviso that at least one of the R¹, R² and R³ radicals is a methoxy or ethoxy radical and X is a propylene radical (—CH$_2$—CH$_2$—CH$_2$—).

Preferably, in the formulae (III) and (IV),

Y is a linear or branched, aliphatic or cycloaliphatic radical having 6 to 13 carbon atoms.

The preferred embodiments specified above for starting component A) likewise apply to the monomeric diisocyanates c).

The invention especially also provides for the use of the inventive compounds containing isocyanate groups and silane groups or of the inventive composition as starting components in the preparation of polyurethanes containing silane groups, or in the production of crosslinkable binders and of crosslinkable raw materials for varnishes, sealants or adhesives. The polyurethanes containing silane groups or crosslinkable binders are preferably used for production of raw materials for varnishes, sealants or adhesives.

The invention further provides polyurethanes containing silane groups, prepared using the inventive compounds containing isocyanate groups and silane groups or the inventive composition.

These can be prepared by reacting the inventive compounds containing isocyanate groups and silane groups or the inventive composition with any desired polyols, preferably at least difunctional polyols, for example simple polyhydric alcohols, ether alcohols or ester alcohols, or standard polymeric polyether polyols, polyester polyols, polycarbonate polyols and/or polyacrylate polyols known from polyurethane chemistry.

EXAMPLES

All percentages are based on weight, unless stated otherwise.

The NCO contents were determined by titrimetric means to DIN EN ISO 11909.

The residual monomer contents were measured to DIN EN ISO 10283 by gas chromatography with an internal standard.

The proportions of bis adduct (formed from two molecules of mercaptosilane and one molecule of diisocyanate) were determined by gel permeation chromatography based on DIN 55672-1 (Gel permeation chromatography (GPC)—Part 1: Tetrahydrofuran (THF) as elution solvent) at room temperature, with the alteration that a flow rate of 0.6 ml/min rather than 1.0 ml/min was employed. The proportions of bis adduct in area % taken from the chromatograms, which were determined with software support, were each equated approximately to proportions in % by weight and reported as such, based on the total amount of mono adduct and bis adduct.

All the viscosity measurements were made with a Physica MCR 51 rheometer from Anton Paar Germany GmbH (DE) to DIN EN ISO 3219.

Example 1 (Inventive)

1680 g (10 mol) of hexamethylene diisocyanate (HDI) were admixed at a temperature of 80° C. under dry nitrogen with 196 g (1.0 mol) of mercaptopropyltrimethoxysilane and, after addition of 0.05 g (25 ppm) of 1,4-diazabicyclo[2.2.2]octane (DABCO), the mixture was stirred for 1 hour until an NCO content of 42.5%, corresponding to a full conversion, had been attained. Subsequently, the unconverted monomeric HDI was removed on a thin-film evaporator at a temperature of 140° C. and a pressure of 0.1 mbar. This gave a virtually colorless, clear isocyanatosilane having the following characteristic data:

NCO content: 11.2%
Monomeric HDI: 0.19%
Viscosity (23° C.): 80 mPas
Proportion of bis adduct: 4.1%

Example 2 (Inventive)

By the process described in example 1, 1008 g (6 mol) of HDI were reacted with 196 g (1.0 mol) of mercaptopropyltrimethoxysilane in the presence of 0.03 g (25 ppm) of DABCO. On attainment of an NCO content of 38.4%, corresponding to full conversion, the unconverted monomeric HDI was removed by thin-film distillation as described in example 1, and a virtually colorless, clear isocyanatosilane was obtained with the following characteristic data:

NCO content: 10.8%
Monomeric HDI: 0.18%
Viscosity (23° C.): 133 mPas
Proportion of bis adduct: 7.0%

Example 3 (Inventive)

By the process described in example 1, 1680 g (10 mol) of HDI were reacted with 180 g (1.0 mol) of mercaptopropylmethyldimethoxysilane in the presence of 0.05 g (25 ppm) of DABCO. On attainment of an NCO content of 42.9%, corresponding to full conversion, the unconverted monomeric HDI was removed by thin-film distillation as described in example 1, and a virtually colorless, clear isocyanatosilane was obtained with the following characteristic data:
NCO content: 11.6%
Monomeric HDI: 0.15%
Viscosity (23° C.): 77 mPas
Proportion of bis adduct: 4.0%

Example 4 (Inventive)

1680 g (10 mol) of hexamethylene diisocyanate (HDI) were admixed under dry nitrogen at a temperature of 80° C. with 238 g (1.0 mol) of mercaptopropyltriethoxysilane and, after addition of 0.05 g (25 ppm) of dibutyltin dilaurate (DBTL), the mixture was stirred for 3 hours until an NCO content of 41.6%, corresponding to full conversion, had been attained. Subsequently, the unconverted monomeric HDI was removed by thin-film distillation as described in example 1, and a virtually colorless, clear isocyanatosilane was obtained with the following characteristic data:
NCO content: 9.9%
Monomeric HDI: 0.15%
Viscosity (23° C.): 92 mPas
Proportion of bis adduct: 4.3%

Example 5 (Inventive)

By the process described in example 4, 2220 g (10 mol) of isophorone diisocyanate (IPDI) were reacted with 196 g (1.0 mol) of mercaptopropyltrimethoxysilane in the presence of 0.06 g (25 ppm) of DBTL. On attainment of an NCO content of 33.0%, corresponding to full conversion, the unconverted monomeric IPDI was removed in a thin-film evaporator at a temperature of 150° C. and a pressure of 0.1 mbar. This gave a virtually colorless, clear isocyanatosilane having the following characteristic data:
NCO content: 9.7%
Monomeric IPDI: 0.23%
Viscosity (23° C.): 5400 mPas
Proportion of bis adduct: 4.8%

Example 6 (Inventive)

By the process described in example 4, 2620 g (10 mol) of 4,4'-diisocyanatodicyclohexylmethane ($H_{12}$-MDI) were reacted with 196 g (1.0 mol) of mercaptopropyltrimethoxysilane in the presence of 0.07 g (25 ppm) of DBTL. On attainment of an NCO content of 28.3%, corresponding to full conversion, the unconverted monomeric $H_{12}$-MDI was removed in a thin-film evaporator at a temperature of 150° C. and a pressure of 0.1 mbar. This gave a virtually colorless, clear isocyanatosilane having the following characteristic data:
NCO content: 8.6%
Monomeric $H_{12}$-MDI: 0.20%
Viscosity (23° C.): 15200 mPas
Proportion of bis adduct: 6.0%

Example 7 (Inventive)

By the process described in example 1, 504 g (3 mol) of HDI were reacted with 196 g (1.0 mol) of mercaptopropyltrimethoxysilane in the presence of 0.02 g (25 ppm) of DABCO. On attainment of an NCO content of 30.0%, corresponding to full conversion, the unconverted monomeric HDI was removed by thin-film distillation as described in example 1, and a virtually colorless, clear isocyanatosilane was obtained with the following characteristic data:
NCO content: 10.0%
Monomeric HDI: 0.21%
Viscosity (23° C.): 143 mPas
Proportion of bis adduct: 13.5%

Example 8 (Comparative)

By the process described in example 1, 336 g (2 mol) of HDI were reacted with 196 g (1.0 mol) of mercaptopropyltrimethoxysilane in the presence of 0.01 g (25 ppm) of DABCO. On attainment of an NCO content of 23.7%, corresponding to full conversion, the unconverted monomeric HDI was removed by thin-film distillation as described in example 1, and a virtually colorless, clear isocyanatosilane was obtained with the following characteristic data:
NCO content: 9.1%
Monomeric HDI: 0.12%
Viscosity (23° C.): 165 mPas
Proportion of bis adduct: 21.0%

The example shows that isocyanatosilanes formed from diisocyanates and mercaptosilanes and prepared using a smaller excess of isocyanate groups than the minimum according to the invention contain very high proportions of 2:1 bis adduct, and for that reason are unsuitable as units for preparation of polyurethanes containing silane groups.

Example 9 (Comparative)

168 g (1.0 mol) of hexamethylene diisocyanate (HDI) were admixed under dry nitrogen at a temperature of 80° C. with 196 g (1.0 mol) of mercaptopropyltrimethoxysilane and, after addition of 0.05 g (25 ppm) of dibutyltin dilaurate (DBTL), the mixture was stirred for 3 hours until an NCO content of 11.5%, corresponding to full conversion, had been attained. This gave a virtually colorless, clear silane-modified isocyanate mixture having the following characteristic data:
NCO content: 11.5%
Monomeric HDI: 5.69%
Viscosity (23° C.):
Proportion of bis adduct: 39.9%

The example shows that the equimolar reaction of a diisocyanate with a mercaptosilane without subsequent thin-film distillation results in a product mixture in which not only the desired 1:1 mono adduct but also high proportions of the 2:1 bis adduct and very high contents of monomeric HDI are present.

Example 10 (Comparative)

To 1680 g (10 mol) of hexamethylene diisocyanate (HDI) at room temperature under dry nitrogen were added 235 g (1.0 mol) of N-butylaminopropyltrimethoxysilane within one hour, and the mixture was stirred for one further hour until an NCO content of 41.7%, corresponding to full conversion, had been attained. Subsequently, the unconverted monomeric HDI was removed on a thin-film evaporator at a temperature of 140° C. and a pressure of 0.1 mbar. This gave a pale yellow, clear isocyanatosilane having the following characteristic data:

NCO content: 5.6%
Monomeric HDI: 1.9%
Viscosity (23° C.): 1000 mPas
Proportion of bis adduct: 47.1%

The example shows that reaction products of isocyanates with secondary aminosilanes behave like blocked polyisocyanates and are redissociated back to the reactants at relatively high temperatures. In spite of an initially high molar excess of HDI, thermal urea cleavage and subsequent recombination in a thin-film evaporator leads to a product mixture containing high proportions of monomeric HDI and HDI/mercaptosilane bis adduct.

Example 11 (Comparative)

To 1680 g (10 mol) of hexamethylene diisocyanate (HDI) at room temperature under dry nitrogen were added 351 g (1.0 mol) of an adduct of aminopropyltrimethoxysilane onto diethyl maleate prepared according to example 5 of EP-A 0 596 360 within one hour, and the mixture was stirred for one further hour until an NCO content of 39.3%, corresponding to full conversion, had been attained. Subsequently, the unconverted monomeric HDI was removed on a thin-film evaporator at a temperature of 140° C. and a pressure of 0.1 mbar. This gave a yellow/brown product having the following characteristic data:

NCO content: 8.3%
Monomeric HDI: 0.12%
Viscosity (23° C.): 470 mPas

The example shows that the isocyanatosilane containing urea groups formed is unstable under the conditions of the thin-film distillation. According to analysis (GPC, $^{13}$C NMR), about 30% of the urea groups originally present in the addition product have reacted by the mechanism described in EP-A 0 807 649 with elimination of ethanol to give hydantoin structures. The HDI obtained as the distillate of the thin-film process is contaminated by HDI ethyl urethanes.

The invention claimed is:

1. A process for preparing compounds containing isocyanate groups and silane groups, comprising reacting at least
    A) 1,6-diisocyanatohexane, 1-isocyanato-3,3,5-trimethyl-5-isocyanatomethylcyclohexane, 2,4'- and/or 4,4'-diisocyanatodicyclohexylmethane or a mixture thereof
    with
    B) at least one mercaptosilane according to formula (I)

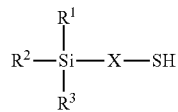

in which
    $R^1$, $R^2$ and $R^3$ are identical or different radicals and each is a saturated or unsaturated, linear or branched, aliphatic or cycloaliphatic radical or an optionally substituted aromatic or araliphatic radical having up to 18 carbon atoms, which may optionally contain up to 3 heteroatoms from the group of oxygen, sulfur, nitrogen, and
    X is a linear or branched organic radical having at least 2 carbon atoms,
    wherein component A) is reacted with component B) in a ratio of equivalents of isocyanate groups to mercapto groups of at least 6:1 to at most 40:1.

2. The process as claimed in claim 1, wherein mercaptosilanes of the general formula (I) or mixtures thereof are used as component B), where
    $R^1$, $R^2$ and $R^3$ are identical or different radicals and each is a saturated, linear or branched, aliphatic or cycloaliphatic radical having up to 6 carbon atoms, which may optionally contain up to 3 oxygen atoms and
    X is a linear or branched alkylene radical having 2 to 10 carbon atoms.

3. The process as claimed in claim 2, wherein mercaptosilanes of the general formula (I) or mixtures thereof are used as component B), where
    $R^1$, $R^2$ and $R^3$ are identical or different radicals and each is an alkyl radical having up to 6 carbon atoms and/or alkoxy radicals containing up to 3 oxygen atoms, with the proviso that at least one of the $R^1$, $R^2$ and $R^3$ radicals is such an alkoxy radical, and
    X is a propylene radical (—$CH_2$—$CH_2$—$CH_2$—).

4. The process as claimed in claim 1, wherein component A) is reacted with component B) in a ratio of equivalents of isocyanate groups to mercapto groups of at least 8:1 to at most 30:1.

5. The process as claimed in claim 1, wherein, after the reaction of components A) with B), any unconverted excess of monomeric diisocyanates A) is removed from the reaction product down to a residual content of less than 1% by weight, based on the total mass of the reaction product.

6. The process as claimed in claim 5, wherein the monomeric diisocyanates are removed by thin-film distillation.

7. A compound containing isocyanate groups and silane groups, obtained by the process as claimed in claim 1.

* * * * *